United States Patent [19]
Furuya

[11] Patent Number: 5,258,788
[45] Date of Patent: Nov. 2, 1993

[54] METHOD FOR MEASURING THE PROTEIN COMPOSITION AND CONCENTRATION IN THE AQUEOUS HUMOR OF THE EYE

[75] Inventor: Yoshiyuki Furuya, Hino, Japan

[73] Assignee: Kowa Company Ltd., Japan

[21] Appl. No.: 866,754

[22] Filed: Apr. 10, 1992

[30] Foreign Application Priority Data

May 29, 1991 [JP] Japan .................. 3-124116

[51] Int. Cl.$^5$ .................. A61B 3/10; A61B 3/117
[52] U.S. Cl. .................. 351/221; 351/246; 128/633; 128/745
[58] Field of Search .............. 351/205, 211, 221, 246; 128/633, 745; 606/4

[56] References Cited

U.S. PATENT DOCUMENTS

| | | | |
|---|---|---|---|
| 4,711,542 | 12/1987 | Ichihashi et al. | 351/221 |
| 4,838,683 | 6/1989 | Ichihashi et al. | 351/221 |
| 4,854,693 | 8/1989 | Ichihashi et al. | 351/221 |
| 4,900,145 | 2/1990 | Akiyama | 351/221 |
| 4,950,068 | 8/1990 | Mizuta | 351/221 X |
| 4,957,360 | 9/1990 | Kakizawa et al. | 351/221 |
| 4,988,184 | 1/1991 | Akiyama | 351/221 |
| 5,000,562 | 3/1991 | Ichihashi et al. | 351/221 |

Primary Examiner—Bruce Y. Arnold
Assistant Examiner—David R. Parsons
Attorney, Agent, or Firm—Bruce L. Adams; Van C. Wilks

[57] ABSTRACT

An ophthalmic measurement method is provided to accurately measure the composition and concentration of protein components in the aqueous humor of the anterior chamber, even when the anterior chamber also contains blood cells. Prior to measuring the autocorrelation function of the intensity of the scattered light from protein components, the anterior chamber is scanned by a laser beam controlled by a control section and the scattered light intensity thereof is measured to determine the location of blood cells by differentiating between light scattered by protein components and light scattered by blood cells. Via an optical scanner, the laser beam is then projected at a position in the anterior chamber from which there has been scattered light from blood cells has not been detected, and the autocorrelation function is measured while the laser beam is stationary.

3 Claims, 3 Drawing Sheets

METHOD FOR MEASURING THE PROTEIN COMPOSITION AND CONCENTRATION IN THE AQUEOUS HUMOR OF THE EYE

BACKGROUND OF THE INVENTION

1. Field of the Invention

The present invention relates to an ophthalmic measurement method, particularly to an ophthalmic measurement method that irradiates the anterior chamber of an eye with a beam of laser light and uses the light scattered by floating protein particles therein to determine protein concentration, composition and the like.

2. Description of the Prior Art

The anterior chamber is located between the cornea and the crystalline lens of the eye, and is filled with aqueous humor. In a normal eye the functioning of the blood-aqueous barrier of the anterior chamber keeps the concentration of albumin, globulin and other such proteins in the aqueous humor at a very low level, and there are no blood cells.

However, when the function of the blood-aqueous barrier is reduced, such as in the aftermath of a white cataract operation, for example, there is an influx of white and red blood cells into the anterior chamber and there is a marked increase in such proteins such as albumin and globulin. For the purpose of post-operative prognoses, it is important to obtain a quantitative measurement of blood cell counts and protein concentrations.

One method of obtaining a quantitative measurement of the protein concentration is to project a laser beam at the protein particles floating in the anterior chamber and measure the intensity of the light scattered by the protein particles.

If the scattering efficiency of the protein particles is A, the concentration of the protein particles in the anterior chamber is N and IO is the intensity of the incident laser beam, then the intensity Is of scattered light from the protein particles will be $$Is = A \times N \times IO \tag{1}$$

It therefore follows that if the scattering efficiency A and the incident laser beam intensity IO are known beforehand, it is possible to obtain the protein concentration N by measuring scattered light intensity Is.

A system apparatus according to the prior art will now be described with reference to FIG. 2. An optical scanner 2 such as a galvanometer mirror is used to scan a beam of laser light from a laser light source 1 one-dimensionally or two-dimensionally in the aqueous humor space of the anterior chamber where the beam is converged by a lens 4. A control section 3 controls the optical scanner 2 so that the laser beam is guided to the appropriate measurement area in the anterior chamber.

An image of the laser beam in the aqueous humor is formed on a mask 6 by a lens 5, and the image of the scanning laser beam in the aqueous humor of the anterior chamber is also scanned on the mask 6. Scattered light passing through the mask aperture is converted to an electrical signal by a photomultiplier 7, and after the signal has been amplified by an amplifier 8 the intensity of the scattered light is analyzed by an analyzer 9.

When the laser beam image is outside the aperture of the mask 6, the system detects a level of noise from external light and also from the dark current of the photomultiplier, while when the laser beam image is within the mask aperture, the signal component is added onto the noise component, as shown in FIG. 3a. The scattering signal proper can therefore be obtained by subtracting the signal intensity obtained when the laser beam is outside the mask aperture from the signal intensity obtained when the laser beam is within the aperture.

In practice there is not just one but a mixture of a multiplicity of floating protein particles in the aqueous humor of the anterior chamber, and as a result equation (1) is actually expressed as $$Is = IO \Sigma Ak \times Nk \tag{2}$$

Here, Ak is the scattering efficiency of protein k and Nk is the concentration of protein k.

As is clear from equation (2), just determining Is will not make it possible to analyze each of the protein components by type. With the composition of each of the multiple protein components being something that is considered to be closely related to the ailment, measuring the composition of each of the multiple protein components in the aqueous humor is of critical significance with respect to diagnosing eye ailments.

One method of determining the composition ratios of protein components involves the application of photon correlation. This technique uses the fact that differences in the diffusion constants of protein components show up as differences in the relaxation times of the scattered light intensity autocorrelation functions, and therefore measures the relaxation times and the weights of the diffusion constants contributing to those relaxation times.

This measurement is usually carried out with the laser beam stationary rather than when it is scanning. However, when using the photon correlation method to obtain the diffusion constant and composition ratio of protein components in the aqueous humor of the anterior chamber, the aqueous humor also contains red and white blood cells with a diameter of around 5 to 20 µm. However, the presence of blood cells in the space scanned by the laser beam gives rise to a signal associated with the scattered light intensity, as shown in FIG. 3b, with the intensity of the scattered light from a blood cell exceeding the intensity of scattered light from protein components.

This type of scattered light degrades the S/N ratio of the autocorrelation function and makes it impossible to achieve an accurate determination of the composition of the protein components.

SUMMARY OF THE INVENTION

An object of the present invention is to provide an ophthalmic measurement method that is able to measure quantities such as the composition and concentration of protein components in the aqueous humor of the anterior chamber, regardless of the presence of red or white blood cells or the like.

In accordance with the present invention, an ophthalmic measurement method is provided in which a laser beam is projected into the aqueous humor of the anterior chamber of the eye and the scattered light from protein components in the anterior aqueous humor is detected to obtain and analyze the autocorrelation function of signals associated with the intensity of the scattered light in order to measure the composition and concentration of protein components in the anterior aqueous humor. The method according to the invention comprises the steps of scanning the anterior chamber by the laser beam to measure the intensity of light scattered therefrom, determining the location of blood cells by distinguishing between scattered light from protein components and scattered light from blood cells, projecting the laser beam at a position in the anterior chamber from which no scattered light from blood cells has been detected, and measuring the autocorrelation function of the intensity of scattered light from protein components while the projected laser beam is stationary.

In accordance with the above arrangement, detection of scattered light from blood cells in the anterior aqueous humor is avoided by controlling the position irradiated by the laser beam, enabling the intensity of scattered light from protein components to be measured and the autocorrelation function thereof to be obtained without being affected by scattered light from the blood cells, thereby improving the S/N ratio of the autocorrelation function.

BRIEF DESCRIPTION OF THE DRAWINGS

The objects and features of the present invention will become more apparent from a consideration of the following detailed description taken in conjunction with the accompanying drawings in which.

DESCRIPTION OF THE PREFERRED EMBODIMENTS

Figure 1:
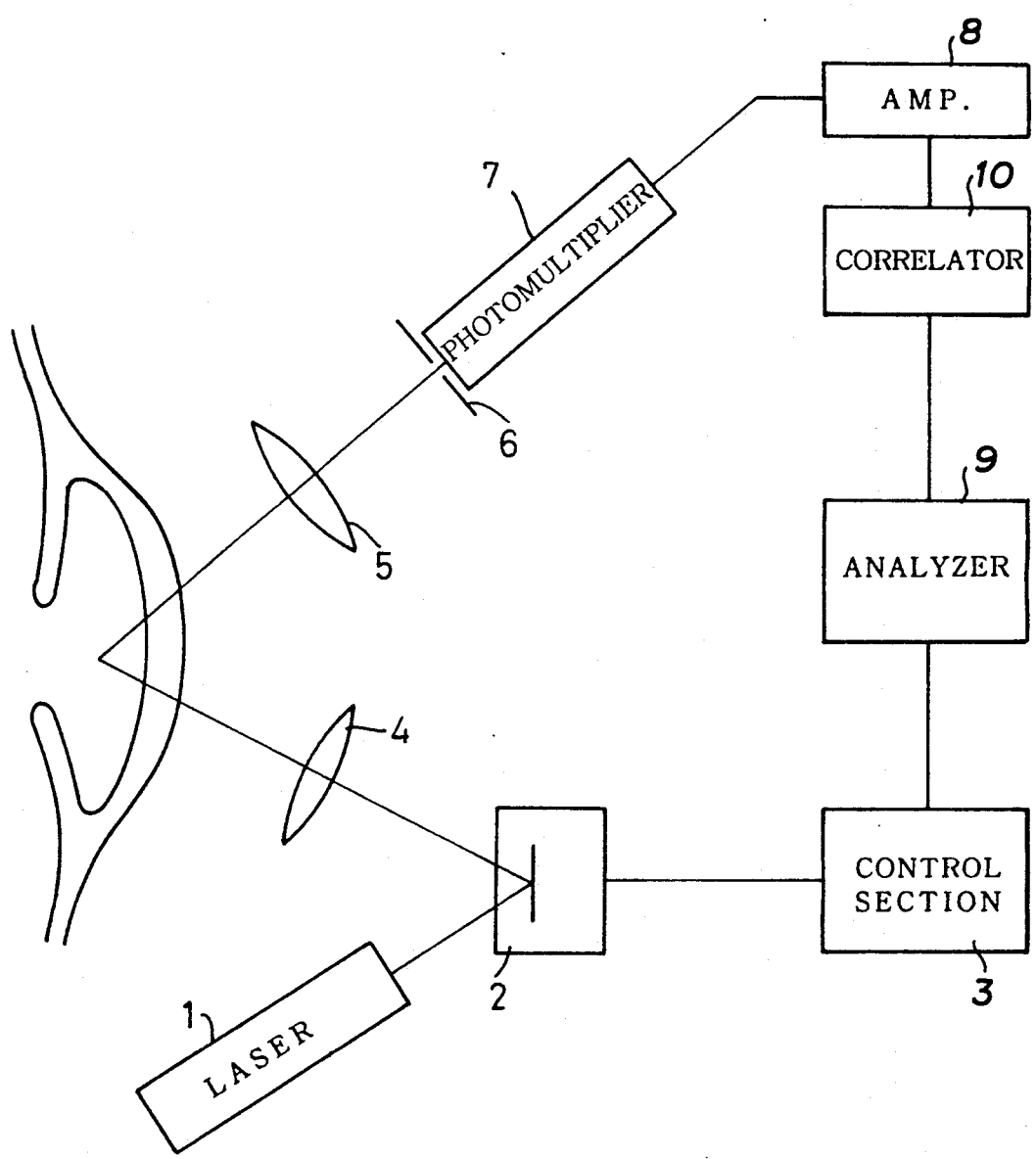
FIG. 1 is a diagram for explaining the ophthalmic measurement method of the present invention.
Figure 2:
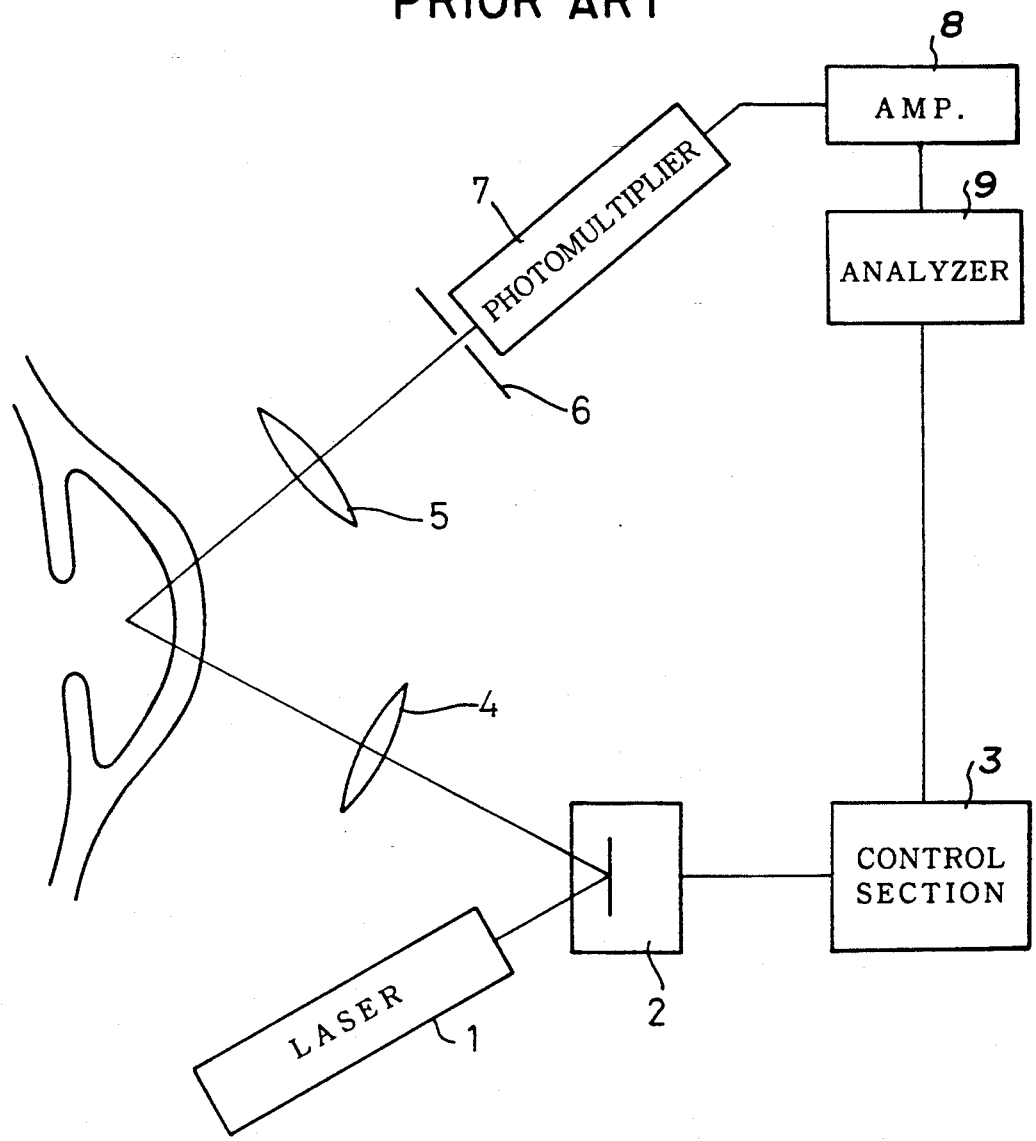
FIG. 2 is a diagram for explaining the ophthalmic measurement method of the prior art.

The invention will now be described in connection with an embodiment as shown in the drawings.

FIG. 1 shows an embodiment of a measurement system according to the present invention. The optical configuration used is the same as a conventional one, with a laser beam being used to scan the aqueous humor of the anterior chamber and scattered light from protein components and blood cells in the aqueous humor being converted to electrical signals.

In this embodiment, the system is provided with a correlator 10 disposed between an amplifier 8 and an analyzer 9. The correlator 10 is used to obtain an autocorrelation function of the intensity of scattered light from protein components in the anterior aqueous humor. Analog and digital control of an optical scanner 2 is effected by a control section 3 in accordance with signals from the analyzer 9, which is used to manually or automatically measure the intensity of scattered light from protein components in the anterior aqueous humor. The control section 3 and analyzer 9 can be constituted by a personal computer or the like.

To measure the autocorrelation function of the intensity of scattered light from protein components in the anterior chamber with the system thus configured, the control section 3 controls the optical scanner 2 to scan the interior of the anterior chamber with a laser beam from a laser light source 1, the intensity of scattered light from protein components and blood cells in the anterior chamber is measured, which scattered light from blood cells is determined and used to calculate the spatial location of those blood cells. The spatial location of blood cells can be detected from the scattered light measured as shown in FIG. 3b.

Figure 3A:
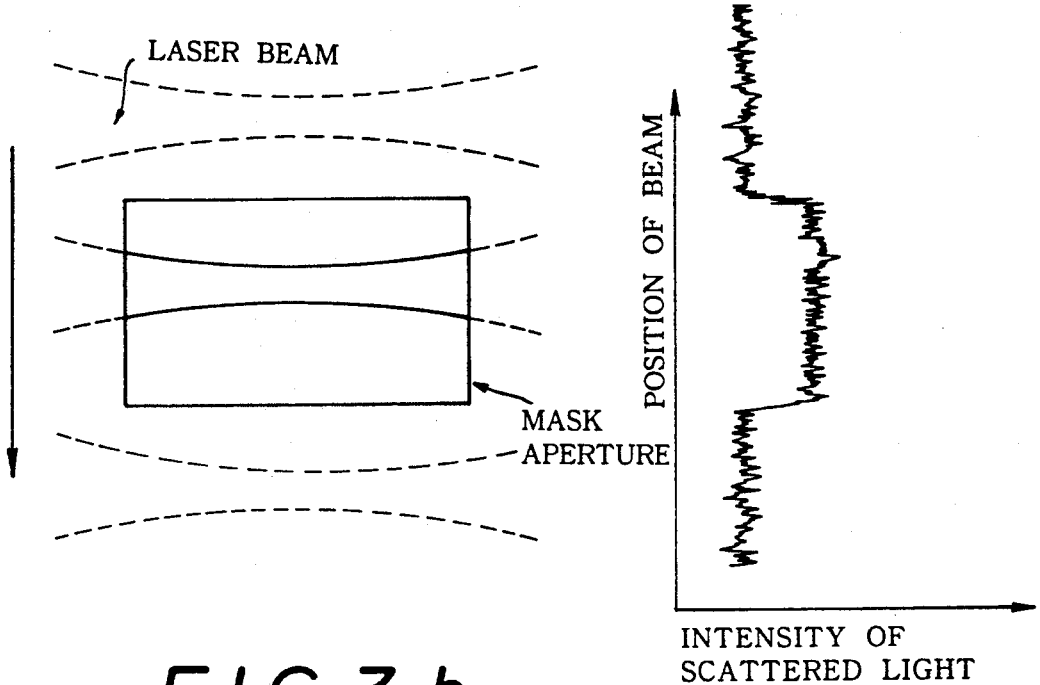
FIGS. 3a and 3b are a diagram for explaining the intensity of scattered light detected by the method of the present invention and by the prior art method.
Figure 3B:
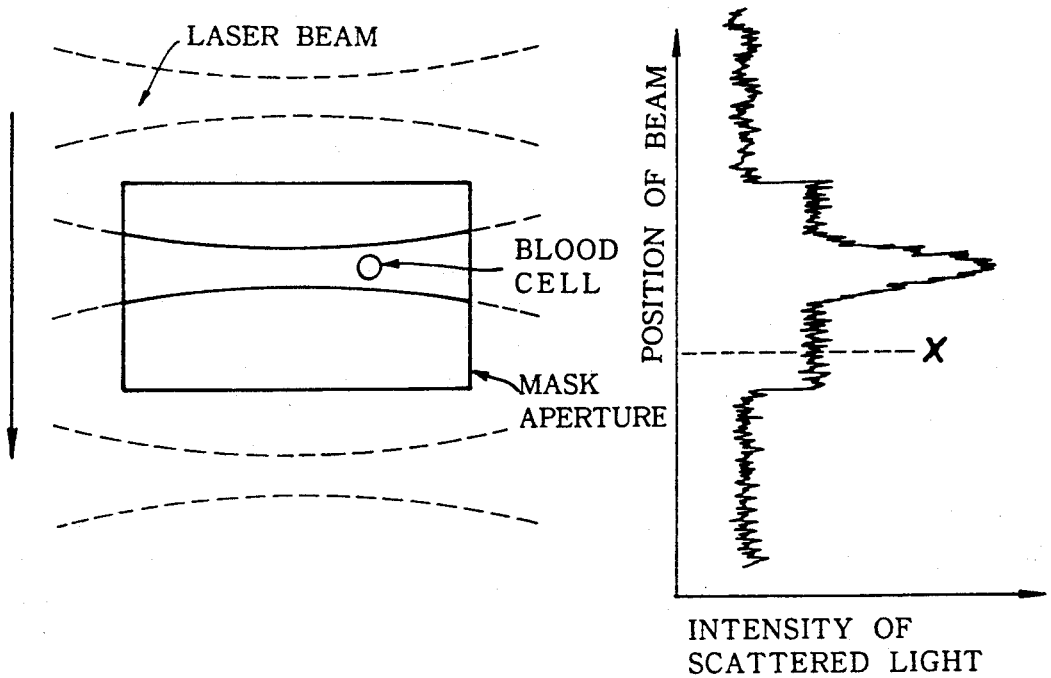

In accordance with signals from the analyzer 9, the optical scanner 2 is controlled by the control section 3 to position the laser beam so the beam is within the mask aperture and directed at a location where there are no blood cells, for example the position denoted by X in FIG. 3b, the autocorrelation function of the intensity of scattered light from protein components in the anterior chamber is measured by the correlator 10, which is done while the laser beam is stationary, as in the conventional method, and based on the measurement results the analyzer 9 determines the composition and concentration of the protein components.

In accordance with this embodiment, therefore, the laser beam is projected at a point where there are no blood cells, so scattered light from protein components in the anterior chamber can be received without receiving scattered light from blood cells. Thus, it is possible to measure the light scattered by the protein components, and as the laser beam is projected at a position in the anterior chamber from which scattered light from blood cells is not received, in obtaining the intensity autocorrelation function of scattered light from the protein components it is possible to detect the scattered light unaffected by the blood cells, thereby enabling the S/N ratio of the autocorrelation function to be improved and the composition and concentration of the protein components to be determined with greater accuracy.

Moreover, obtaining the correlation function by means of a hardware-based correlator 10 system rather than by using a software-based analyzer 9 makes it possible to carry out high-speed real-time correlation computation without burdening the analyzer 9.

The laser beam position X shown in FIG. 3b may be obtained by finding the point at which, when the laser beam is within the mask aperture, the intensity of the scattered light is at its lowest.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is

1. An ophthalmic measurement method in which a laser beam is projected into the aqueous humor of the anterior chamber of the eye and the scattered light from protein components in the anterior aqueous humor is detected to obtain and analyze the autocorrelation function of signals associated with the intensity of the scattered light in order to measure the composition and concentration of protein components in the anterior aqueous humor, comprising the steps of:

scanning the anterior chamber by the laser beam to measure the intensity of light scattered therefrom;

determining the location of blood cells by distinguishing between scattered light from protein components and scattered light from blood cells;

projecting the laser beam at a position in the anterior chamber from which no scattered light from blood cells has been detected; and measuring the autocorrelation function of the intensity of scattered light from protein components while the projected laser beam is stationary.

2. An ophthalmic measurement method according to claim 1, wherein the laser beam is projected at a point at which the intensity of the scattered light is at its lowest.

3. An ophthalmic measurement method according to claim 1, wherein the autocorrelation function is measured by a correlator provided separately from means for measuring the composition and concentration of protein components in the anterior aqueous humor.

* * * * *